United States Patent
Sabol (10) Patent No.: US 7,638,095 B2
(45) Date of Patent: Dec. 29, 2009

(54) PERSONAL PORTABLE BLOOD GLUCOSE METER WITH REPLACEABLE CARTRIDGE OF TEST STRIPS

(75) Inventor: Peter Sabol, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 514 days.

(21) Appl. No.: 11/276,043

(22) Filed: Feb. 10, 2006

(65) Prior Publication Data
US 2007/0189928 A1   Aug. 16, 2007

(51) Int. Cl.
*G01N 33/48* (2006.01)
(52) U.S. Cl. .............. 422/68.1; 422/82.03; 422/66; 422/87; 204/416
(58) Field of Classification Search .............. 422/68.1, 422/56, 58, 61, 63, 65, 99, 82.05, 102; 436/43, 436/46, 180; 204/406, 407
See application file for complete search history.

(56) References Cited

U.S. PATENT DOCUMENTS

| | | |
|---|---|---|
| 3,526,480 A | 9/1970 | Findl et al. |
| 4,218,421 A | 8/1980 | Mack, Jr. et al. |
| 4,328,184 A | 5/1982 | Kondo |
| 4,883,642 A | 11/1989 | Bisconte |
| 4,995,402 A | 2/1991 | Smith et al. |
| 5,047,044 A | 9/1991 | Smith et al. |
| 5,077,010 A | 12/1991 | Ishizaka et al. |
| 5,178,835 A | 1/1993 | Uekusa et al. |
| 5,228,972 A | 7/1993 | Osaka et al. |
| 5,279,294 A * | 1/1994 | Anderson et al. ........... 600/322 |
| 5,510,266 A | 4/1996 | Bonner et al. |
| 5,679,311 A | 10/1997 | Harttig et al. |
| 5,686,829 A | 11/1997 | Girault |
| 5,997,817 A | 12/1999 | Crismore et al. |
| 6,009,632 A * | 1/2000 | Douglas ........................ 33/562 |
| 6,027,689 A * | 2/2000 | Markart ........................ 422/58 |
| 6,488,891 B2 | 12/2002 | Mason et al. |
| 7,323,141 B2 * | 1/2008 | Kirchhevel et al. ........ 422/68.1 |
| 7,378,270 B2 * | 5/2008 | Azarnia et al. ........... 435/287.2 |
| 2002/0188224 A1* | 12/2002 | Roe et al. ................... 600/584 |

(Continued)

FOREIGN PATENT DOCUMENTS

DE           19819407 A1     11/1999

(Continued)

OTHER PUBLICATIONS

International Patent Application PCT/EP2007/001113 International Search Report mailed Jul. 10, 2007.

*Primary Examiner*—Robert J Hill, Jr.
*Assistant Examiner*—Dwan A Gerido
(74) *Attorney, Agent, or Firm*—Woodard, Emhardt, Moriarty, McNett & Henry (57) ABSTRACT

A test meter system includes a cartridge that houses a test strip tape, which includes a plurality of test elements, and the cartridge defines a meter opening. The cartridge further incorporates an indexing mechanism for indexing the test strip tape. A meter is configured to analyze body fluid via the test strip tape, and the meter includes a display for displaying test results as well as other information. At least a portion of the meter is received in the meter opening of the cartridge to provide a compact configuration. In one form, the test strip system has a generally cylindrical outer shape to provide a pleasing handheld shape.

31 Claims, 9 Drawing Sheets

U.S. PATENT DOCUMENTS

2003/0211619 A1   11/2003   Olson et al.
2005/0214881 A1 * 9/2005   Azarnia et al. ............. 435/7.92

FOREIGN PATENT DOCUMENTS

| DE | 19849539 A1 | 5/2000 |
|---|---|---|
| DE | 19857426 A1 | 6/2000 |
| EP | 1 286 162 A2 | 2/2000 |
| JP | 1105157 A1 | 4/1989 |
| JP | 5045363 A1 | 2/1993 |
| WO | WO 01/23885 A1 | 4/2001 |
| WO | WO 02/08753 A2 | 1/2002 |
| WO | WO 2005/047861 A1 | 5/2005 |

* cited by examiner

PERSONAL PORTABLE BLOOD GLUCOSE METER WITH REPLACEABLE CARTRIDGE OF TEST STRIPS

BACKGROUND

The present invention generally relates to biological fluid testing and more specifically, but not exclusively, concerns a portable meter with a replaceable cartridge of test strips that has a compact and pleasing handheld shape.

The acquisition and testing of biological fluids is useful for many purposes and continues to grow in importance for use in medical diagnosis and treatment, such as for diabetes, and in other diverse applications. In the medical field, it is desirable for lay operators to perform tests routinely, quickly, and reproducibly outside of a laboratory setting, with rapid results and a readout of the resulting test information. Testing can be performed on various body fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

The testing of body fluids basically involves the steps of obtaining the fluid sample, transferring the sample to a test device, conducting a test on the fluid sample, and displaying the results. Performing these steps can be difficult for patients, especially for patients with limited hand dexterity, such as the elderly, or those suffering the affects of their condition, like diabetes. Diabetics suffer many symptoms that can make self-monitoring difficult. For example, diabetics can sometimes experience numbness or tingling in their extremities, such as their hands, which can make handling individual test strips difficult. To address some of these issues, cassettes and drums containing multiple test strips have been developed that dispense the test strips on an individual basis. However, it has been found that such meter designs are rather bulky and hard to handle. For instance, a typical design requires that the cassette or drum is loaded inside a meter that contains the electronics for analyzing the sample. With the size of electronics becoming smaller by the day, a significant amount of space in the meter may simply now be empty, which tends to make the meter larger than it has to be. Although technically portable, these types of meters are not practically portable because they are not small enough to discretely fit inside a shirt or pants pocket. Thus, there remains a need for further contributions in this area of technology.

SUMMARY

One aspect concerns a portable test meter system. The test meter system includes a cartridge that houses a test strip tape, which includes a plurality of test elements, and the cartridge defines a meter opening. A meter is configured to analyze body fluid via the test strip tape. At least a portion of the meter is received in the meter opening of the cartridge to provide a compact configuration.

Another aspect relates to a test strip cartridge. The test strip cartridge includes a housing that is ring shaped. The housing defines a meter opening configured to receive at least a portion of a meter. A test strip tape is wrapped around the meter opening of the housing, and the test strip tape includes a plurality of test strip elements configured to analyze body fluid. The housing defines a sampling portion where the test elements collect the body fluid. An indexing mechanism is coupled to the housing to index the test elements to the sampling portion.

A further aspect concerns a meter that includes an insertion portion configured to extend through a meter opening in a cartridge. An alignment key member extends from the insertion portion. The alignment key member includes one or more contacts. The alignment key member is configured to align the contacts with the cartridge. A stop flange extends from one end of the insertion portion.

Further forms, objects, features, aspects, benefits, advantages, and embodiments of the present invention will become apparent from a detailed description and drawings provided herewith.

DESCRIPTION OF THE SELECTED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail, although it will be apparent to those skilled in the relevant art that some features that are not relevant to the present invention may not be shown for the sake of clarity. It should be noted that directional terms, such as "up", "down", "top" and "bottom", are used herein solely for the convenience of the reader in order to aid in the reader's understanding of the illustrated embodiments, and it is not the intent that the use of these directional terms in any manner limit the described, illustrated, and/or claimed features to a specific direction or orientation.

As will be described in greater detail below, an annular or ring-shaped test strip cartridge, according to one embodiment, includes a sealed plastic annular compartment containing a tape that has a series of test strip sensors for testing body fluid properties, such as blood glucose levels. In one form, the ring-shaped test strip cartridge is coupled to a similarly shaped annular meter in a side-by-side fashion similar to that of a margarine container lid. In another form, the annular compartment is coupled to the annular meter in a side-by-side fashion via a locking key. The meter includes electronics for analyzing the fluid sample and a display for displaying the results from the analysis. To provide a compact design, all or part of the electronics of the meter can be provided in a portion of the meter that is disposed inside the ring-shaped cartridge when the meter and cartridge are coupled together. The cartridge can also have a carbon ink electrical pattern so that the meter can identify the lot coding. Alternatively or additionally, the cartridge can have an Electrically-Erasable Programmable Read-Only Memory (EEPROM) that is electrically coupled to the meter for sensor coding purposes or can have a Radio Frequency Identification (RFID) tag. The overall annular shape of the meter-cartridge assembly has a pleasing handheld shape.

The cartridge can incorporate a seal that minimizes the risk of test strip contamination, and further, the tape can incorporate a clear cover tape. In one embodiment, the annular compartment incorporates an integral advancement mechanism for advancing the reel of test strips. In one form, the advancement mechanism grips side notches formed between the individual sensors, and in another form, the advancement mechanism grips the top of the tape of strips. In one example, the test strip sensors are electrochemical test strips with a pair of holes formed on the bottom of each sensor so that the meter can couple to the electrodes in the test strip. The top side of each test strip includes a sample cavity that opens to one side and electrodes with a reagent for analyzing the fluid sample. Each test strip can have a finger relief notch that conforms to the shape of the finger such that the fluid sample can be easily collected.

Figure 1:
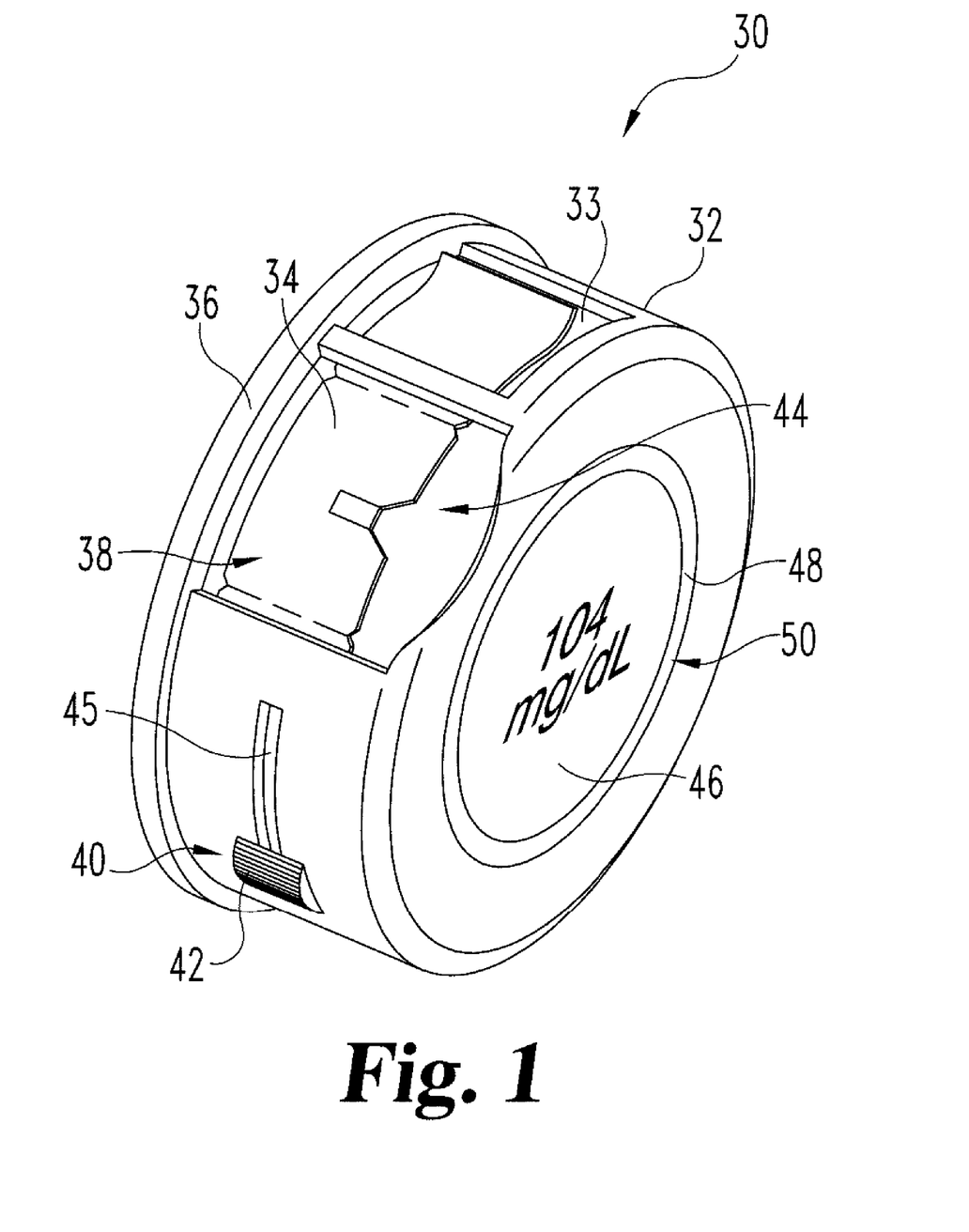
FIG. 1 is a perspective view of a portable meter system according to one embodiment.
Figure 2:
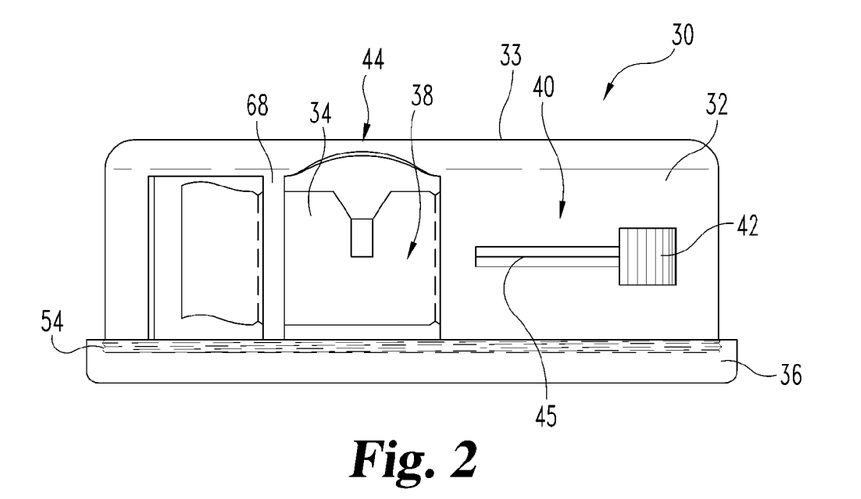
FIG. 2 is a top view of the FIG. 1 meter system.
Figure 3:
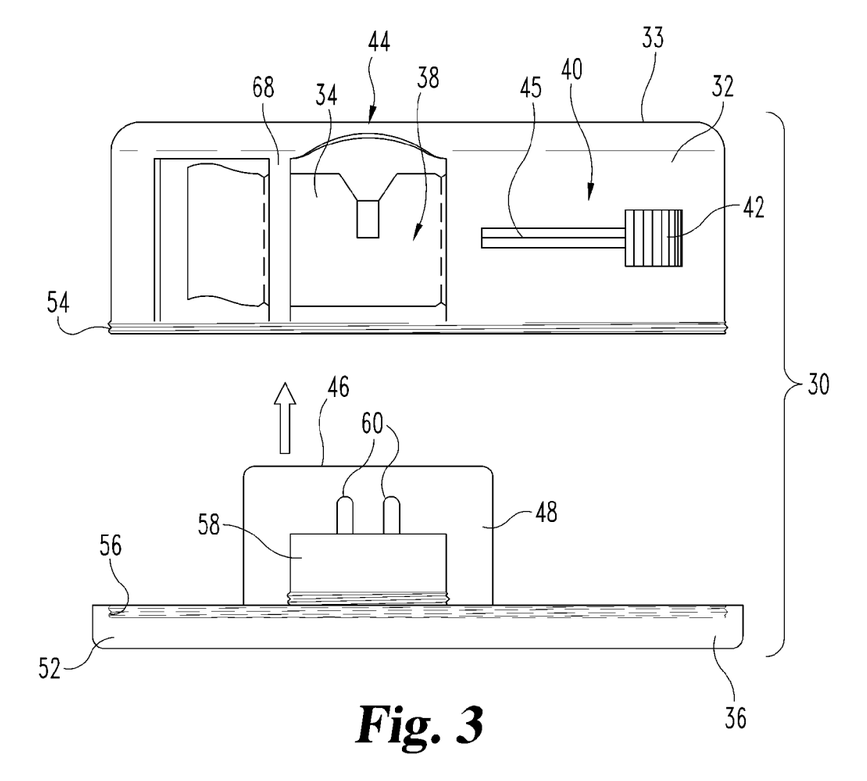
FIG. 3 is an exploded view of the FIG. 1 meter system.

A portable meter system 30 according to one embodiment (among many possible embodiments) is illustrated in FIGS. 1, 2, and 3. Although the portable meter system 30 will be described with reference to portable blood glucose testing, it should be appreciated that the meter system 30 can be adapted to test a wide variety of biological fluids and fluid properties. Looking at FIGS. 1 and 2, the meter system 30 includes a cartridge 32 with a cartridge housing 33 that houses one or more test strip elements (biosensors) 34 and a meter 36 that is coupled to the cartridge 32 for providing the test results from the test strips 34. The test strips 34 are housed inside the cartridge 32 in a side-by-side manner on a test strip tape 38. The cartridge 32 further includes an index or advancement mechanism 40 with an index or advancement button 42 for advancing unused test strips 34 on the tape 38 to a sampling portion or area 44 on the cartridge housing 33. The sampling portion 44 in the embodiment shown is in the form of a cavity or notch in the housing 33, but the sampling portion 44 can be shaped differently in other embodiments. To advance the test strips 34, the index button 42 is pressed down and pushed along an advancement slot 45. In other embodiments (not shown), the advancement mechanism 40 can include a motor or other powered mechanism that advances the tape 38 at the user's command, or an automatic mechanism that advances the tape 38 automatically after a test strip 34 has been used. In the illustrated embodiment, the meter 36 includes a display 46 for displaying test results as well as other information. It should be appreciated that the meter 36 can include other output devices, like a speaker, for example.

Figure 4:
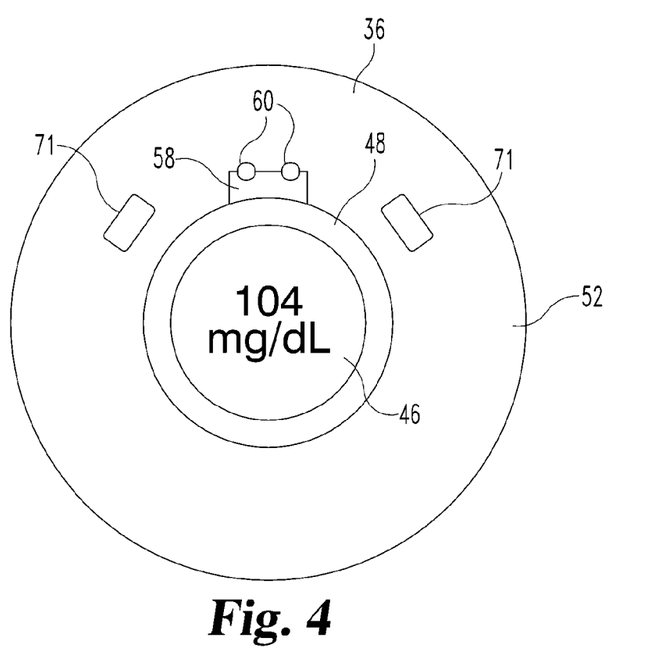
FIG. 4 is a front view of a meter used in the FIG. 1 meter system.
Figure 5:
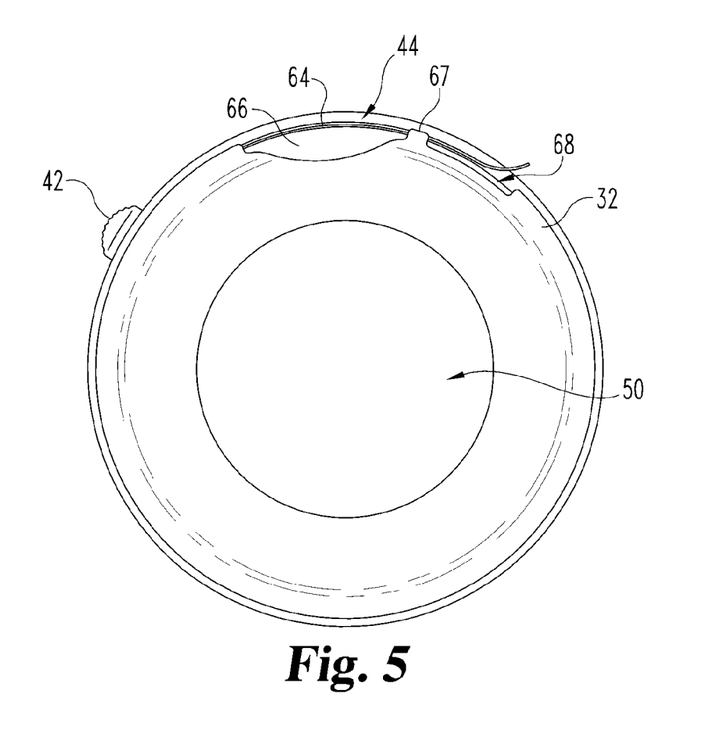
FIG. 5 is a front view of a cartridge used in the FIG. 1 meter system.

As can be seen, the meter system 30 has a compact design that allows for easy storage and handling. In particular, the meter system 30 has an overall cylindrical or hockey puck shape that allows the meter system 30 to be easily gripped and handled. The rounded shape of the meter system 30 allows those with hand dexterity problems, such as the elderly, to easily grip and use the meter system 30. As mentioned before, most typical cassette or cartridge designs have the cassette received inside a meter, which tends to waste space, especially in view of recent reductions in the size of the electronics used in meters. To have a compact design, the meter system 30 in FIG. 1 generally takes the opposite approach by having the majority of the meter 36 housed within the cartridge 32. With reference to FIGS. 3, 4, and 5, the meter 36 includes a projection or shaft 48 that is received inside a meter opening 50 in the cartridge 32, which is provided with a complimentary configuration matching the projection 48. As depicted, the projection 48 on the meter 36 extends completely through the cartridge 32. In the illustrated embodiment, the projection 48 and the meter opening 50 are generally cylindrical in shape, but in other embodiments, the projection 48 and the meter opening 50 can be shaped differently. For example, when viewed on end, instead of a generally circular shape, the projection 48 can have a polygonal shape, and the meter opening 50, of course, having a complimentary configuration to receive such a projection 48.

At one end of the projection 48 in FIGS. 3 and 4, the meter 36 has a stop or engagement flange 52 against which a side of the cartridge 32 rests, and the display 46 is positioned at the other end of the projection 48. With the display 46 on the end of the projection 48, the user can readily view the display 46 when the meter system 30 is gripped in the hand of the user. It is contemplated that the display 46 can be disposed elsewhere in the meter system 30. For instance, the display 46 can be located on the stop flange 52 of the meter 36 on the side opposite the projection 48, and in another embodiment, the meter 36 has the display 46 on both the projection 48 and the stop flange 52. As should be recognized, the meter 36 can have a different overall shape than the one shown in the drawings. By way of a nonlimiting example, the stop flange 52 can be eliminated so that the entire meter 36 fits inside the meter opening 50 of the cartridge 32.

In the illustrated embodiment, the cartridge 32 is coupled to the meter 36 in a fashion similar to a lid of a margarine container. On the side facing the meter 36, the cartridge 32 has around its periphery a flexible coupling flange 54 that engages with a coupling groove 56 on the stop flange 52 of the meter 36. Once engaged, a snap fit is created between the cartridge 32 and the meter 36. To remove the cartridge 32 from the meter 36, the coupling flange 54 is pried from the coupling groove 56. In one form, the stop flange 52 has a coin slot that can be used in prying the cartridge 32 from the meter 36. In another form, the coupling flange 54 has a weakened portion that allows the flange 54 to be torn off the cartridge 32 in order to release the cartridge 32 from the meter 36. It is envisioned that the cartridge 32 can be coupled to the meter 36 in other manners. For example, the cartridge 32 and meter 36 in another embodiment can be coupled together through a locking key or bayonet type locking mechanism.

To operatively couple and align the meter 36 with the test strips 34 in the sampling portion 44, the meter 36 has a contact support or alignment key member 58 that extends from the projection 48. The alignment key member 58 has one or more contacts 60 that are constructed and arranged to connect with contacts on a test strip 34 when positioned in the sampling portion 44. In one form, the contacts 60 include leaf springs with bent ends that are biased to contact the test strip 34, but other embodiments can include other types of contacts 60. Further, the meter 36 in other embodiments can include more or less contacts 60 than are shown in the drawings. In the illustrated embodiment, the contacts 60 on the meter 36 directly engage the contacts on the test strip 34. Nevertheless, the contacts 60 on the meter 36 can indirectly connect to the contacts on the test strip 34 in other embodiments. As an example, the sampling portion 44 of the cartridge 32 in another embodiment is sealed from the meter 36 so as to minimize the chance of the meter 36 being contaminated with body fluid. In this example, the sampling portion 44 includes intermediate contacts that are disposed between the contacts 60 on the meter 36 and those on the test strip 34 in order to complete the electrical connection between the meter 36 and the test strip 34. Moreover, when other types of test strips are used that do not require an electrical connection, like optical test strips, non-contact sensors such as optical sensors can be used in place of the contacts 60 on the meter 36.

Figure 6:
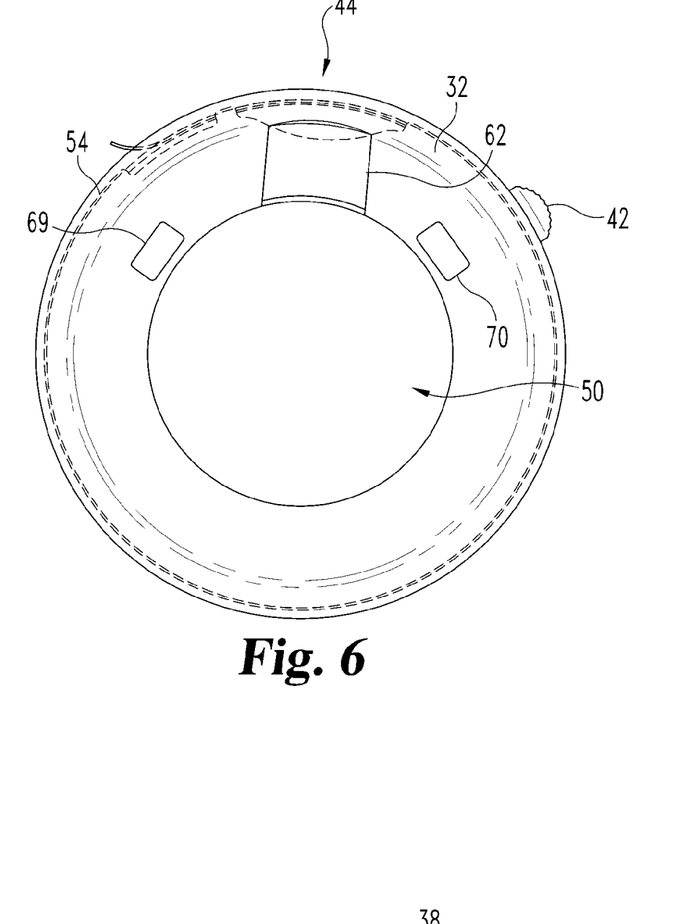
FIG. 6 is a back view of the FIG. 5 cartridge.

Looking at FIG. 6, the side of the cartridge 32 that faces the meter 36 has an alignment key notch 62 that is configured to receive the alignment key member 58 on the meter 36. In the illustrated embodiment, the alignment key notch 62 is only located on one side of the cartridge 32. However, it is contemplated that the alignment key notch 62 can be positioned on both sides of the cartridge 32 so that the user can attach the meter 36 to either side of the cartridge 32, which in turn allows the user to comfortably grip the meter system 30 in either hand. As depicted, the notch 62 is positioned near the sampling portion 44 so that the contacts 60 are properly aligned inside the sampling portion 44.

Turning to FIG. 5, the sampling portion 44 has a guide surface 64 that guides the test strip tape 38 in the sampling portion 44. At the sampling portion 44, the cartridge 32 has a contoured relief notch or indentation 66 that has a concave shape to match the contour of the finger or some other body part. As illustrated in this embodiment, the cartridge 32 can have a tear bridge 67 for tearing off used test strips 34 from the test strip tape 38, and a tear cavity 68 where the used test strips 34 are torn from the test strip tape 38. Instead of disposing of the used test strips 34 in an individual manner, the used test strips 34 can, in an alternative embodiment, remain attached to the test strip tape 38 and stored in a separate disposal compartment within the cartridge 32 in other embodiments. Thus, once all of the test strips 34 are used, the entire cartridge 32 containing all of the used test strips 34 can be disposed of at one time.

To calibrate the meter 36, the cartridge 32 in the embodiment shown in FIG. 6 includes an electronic identifier 69, like an EEPROM and/or an RFID tag, and non-evident coding 70, like a barcode, a carbon ink electrical pattern, or other machine-readable representations of information, which contains lot specific information about the test strip tape 38. In the embodiment shown, the electronic identifier 69 and the non-evident coding 70 are located on the side of the cartridge 32 that faces the meter 36 when coupled together. However, the electronic identifier 69 and/or the non-evident coding 70 can be located elsewhere on the cartridge 32. With reference to FIG. 4, the meter 36 has sensors 71 located at corresponding positions on the stop flange 52 so as to be able to read the information from the electronic identifier 69 and the non-evident coding 70. By way of example, the sensors 71 can include electrical contacts, optical sensors, and/or an RFID reader, to name a few. As should be understood, the sensors 71 can also be positioned at locations different from the ones shown in the drawings. For instance, an RFID reader does not have to be located directly next to an RFID tag on the cartridge 32.

Figure 8:
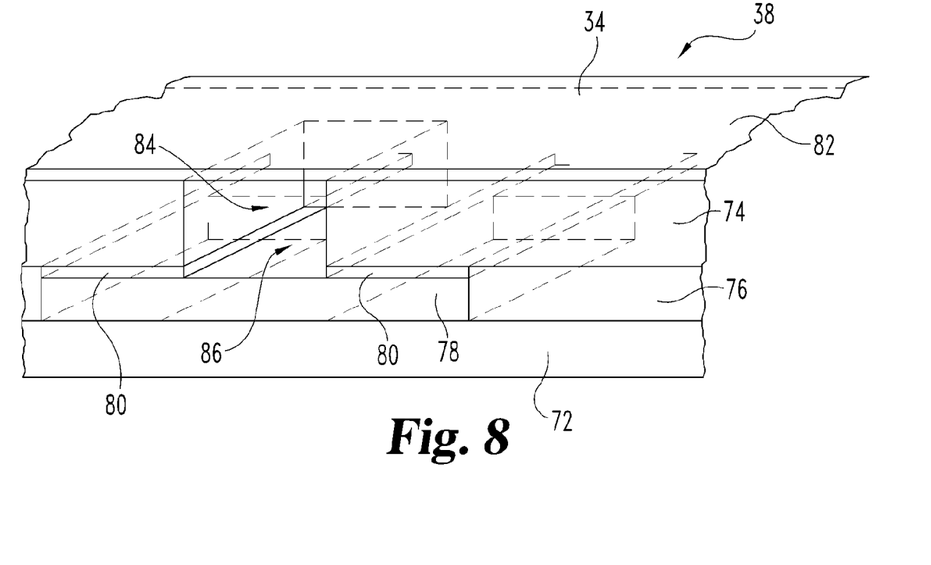
FIG. 8 is a perspective view of the FIG. 7 test strip tape.
Figure 9:
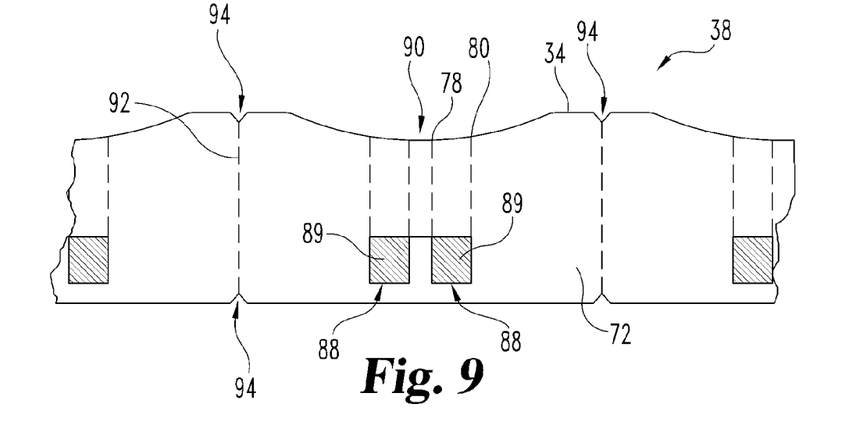
FIG. 9 is a bottom view of the FIG. 7 test strip tape.
Figure 10:
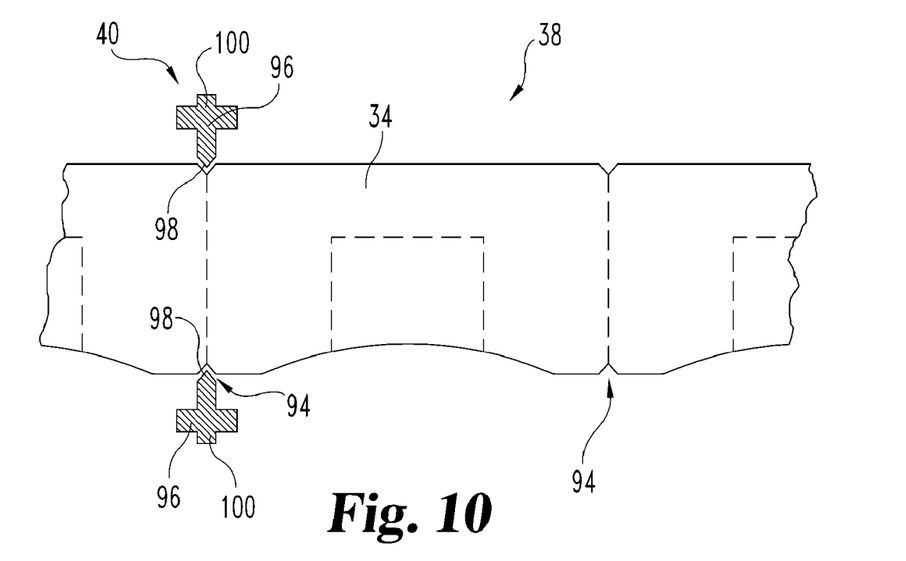
FIG. 10 is a partial, top cross sectional view of an indexing mechanism according to one embodiment.

In the illustrated embodiment, the unused portion of the test strip tape 38 is wrapped around in a spiral manner within the cartridge 32. However, the test strip tape 38 can be stored in a different manner in other embodiments. For instance, the test strip tape 38 can be attached to and wrapped around a reel within the cartridge 32. FIGS. 8, 9, and 10 show a top plan view, a front perspective view, and a bottom plan view of the test strip, respectively. The test strip 34 in the FIG. 1 meter system 30 has been described with reference to an electrochemical test strip, but it should be understood that the meter system 30 can be modified to utilize other testing means, like optical test strips. For the sake of clarity as well as brevity, the various components of the test strip 34 and techniques for manufacturing the test strip 34 will not be described in great detail below, but reference is made to U.S. Patent Application Publication Nos.: 2005/0008537 A1 to Mosoius et al., published Jan. 13, 2005 (U.S. application Ser. No. 10/871,966, filed Jun. 18, 2004); 2005/0013731 A1 to Burke et al., published Jan. 20, 2005 (U.S. application Ser. No. 10/871,468, filed Jun. 18, 2004); 2005/0016844 A1 to Burke et al., published Jan. 27, 2005 (U.S. application Ser. No. 10/871,673, filed Jun. 18, 2004); 2005/0019212 A1 to Bhullar et al., published Jan. 27, 2005 (U.S. application Ser. No. 10/872,027, filed Jun. 18, 2004); and 2005/0103624 A1 to Bhullar et al., published May 19, 2005 (U.S. application Ser. No. 10/871, 937, filed Jun. 18, 2004), which are hereby incorporated by reference in their entirety.

Referring to FIG. 8, the test strip 34 includes a bottom (first) substrate or layer 72, a top (second) substrate or layer 74, and a sealer/adhesive layer 76 that joins the bottom 72 and top 74 substrates together. In one embodiment, the bottom 72 and top 74 substrates are made from MELINEX® (E.I. DuPont de Nemours and Company of Wilmington, Del.). The sealer/adhesive 76 serves as a spacer between the bottom 72 and top 74 substrates. Between the substrates 72, 74, the test strip 34 further includes a reagent layer 78 and electrodes 80. As shown, the electrodes 80 are positioned on the bottom surface of the top substrate 74, and the electrodes 80 are spaced apart in a generally parallel manner. The electrodes 80 can includes various combinations of working, counter, and/or reference electrodes. In conjunction with the reagent 78, the electrodes 80 are configured to detect the presence of, and/or measure the concentration of, at least one analyte by way of electrochemical oxidation and reduction reactions. These reactions are converted to an electrical signal that can be correlated to an amount or concentration of the analyte, such as via coulometric, amperometric, voltammetric, and other techniques. Again, it should be recognized that the fluid sample in other embodiments can be analyzed in other manners, such as through optical techniques.

Opposite the electrodes 80, a cover layer or film 82 is attached to the top surface of the top substrate 74. The top substrate 74 defines a sample notch or cutout 84 that, along with the reagent 78, electrodes 80, and cover layer 82, forms a sample channel or chamber 86 in which body fluid is drawn for analysis. In the embodiment shown, the sample chamber 86 is sized and configured to draw the fluid via capillary action, but it should be understood that the fluid can be drawn in other manners, like via a vacuum. The electrodes 80 in FIG. 8 are generally flush with the walls of the sample chamber 86, but in other embodiments, the electrodes 80 can be positioned elsewhere. In one form, as the fluid sample is collected, the sample contacts just the edges of the electrodes 80 that are flush with the walls of the sample chamber 86, but the sample in other forms can soak into the reagent and contact the underside of the electrodes 80. For example, the reagent layer 78 in another form includes a mesh or other matrix material that allows the sample to soak in from the sample chamber 86 and contact the electrodes 80 from the underside. In yet another embodiment, the test strip 34 does not have a sample chamber 86, but rather, the reagent layer 78 includes a mesh material that wicks the fluid sample into the reagent layer 78 via capillary action so that the sample can be applied to the underside of the electrodes 80.

The cover layer 82 in whole or part can be transparent or semitransparent to allow the user to see if the sample chamber 86 has been sufficiently filled for analysis. In the illustrated embodiment, the cover layer 82 is a transparent film so that the user can view sample fill sufficiency in the sample chamber 86. In other embodiments, the cover layer 82 incorporates a combination of transparent, semi-transparent, and opaque portions, and alternatively, the cover layer 82 can be completely opaque. Although not shown in the drawings, it should be appreciated that the test strip 34 can incorporate a vent opening for venting air or other gases from the sample chamber 86.

Looking at FIG. 9, the bottom substrate 72 defines one or more contact openings 88 that create contacts 89 on the underside of the electrodes 80. The reagent layer 78 ends at the contact openings 88 so that the contacts 89 of the electrodes 80 are exposed. The contacts 89 on the electrodes 80 are configured to contact the corresponding contacts 60 on the meter 36 either directly or indirectly. The FIG. 9 embodiment shows a pair of contact 89 that are spaced apart generally the same distance as the contacts 60 on the meter 36, but it should be appreciated that the test strip 34 can include more or less contacts 89 than are shown. When the test strip tape 38 is loaded in the cartridge 32, the contacts 89 face radially inward relative to the cartridge 32 so that the contacts 60 of the meter 36 are positioned radially inwards relative to the cartridge 32, thereby allowing all or part of the meter 36 to be positioned inside the cartridge 32. This in turn gives the meter system 30 its compact design. It, however, is contemplated that the contacts 89 can be located at other places on the test strip 34. In another embodiment, for example, the electrodes 80 can extend across the entire width of the test strip 34 such that contacts 89 are formed along the side edges of the test strip 34.

Figure 7:
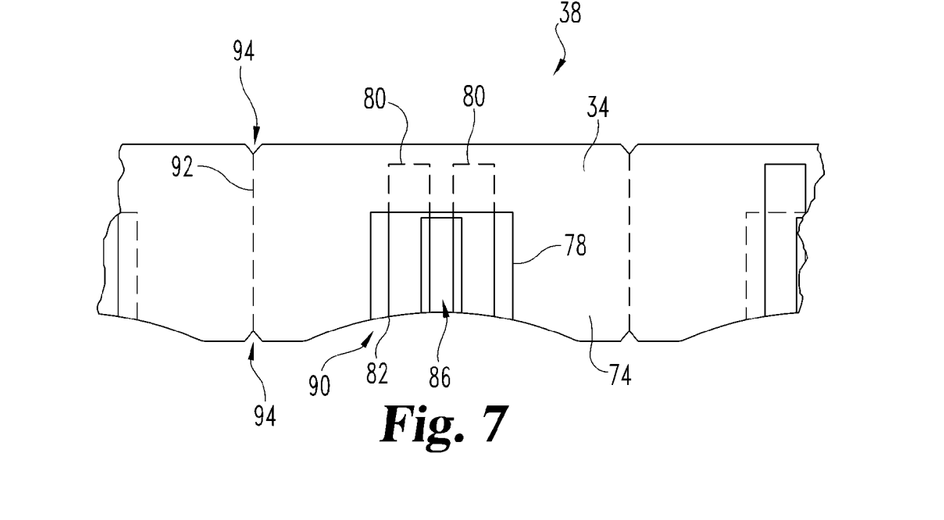
FIG. 7 is a top view of a test strip tape used in the FIG. 5 cartridge.

Near the opening of the sample chamber 86, each test strip 34 in the embodiment shown in FIG. 7 has a curved relief notch 90 that conforms to the shape of the finger or other body part. As mentioned before, the cartridge 32 likewise includes a curved relief notch or surface 66. Together the relief notch 66 on the cartridge 32 and the relief notch 90 on the test strip 34 cooperate to make sampling easier for the user. Nevertheless, it is envisioned that the relief notches 66, 90 can be optional in other embodiments.

Between each test strip 34, the test strip tape 38 has weakened sections or break lines 92 that allow individual test strips 34 to be detached for disposal or other purposes. In other embodiments, such as the embodiment in which the used test strips 34 are housed in the cartridge 32, the break lines 92 can be optional. To advance the test strips 34, the test strip tape 38 has opposing engagement notches 94 that are engageable with the indexing mechanism 40. In the illustrated embodiment, the engagement notches 94 are aligned with the break lines 92 to further weaken the connections between the individual test strips 34. As should be realized, the test strip tape 38 can include other types of engagement structures for engaging the indexing mechanism 40, besides the one illustrated.

Figure 11:
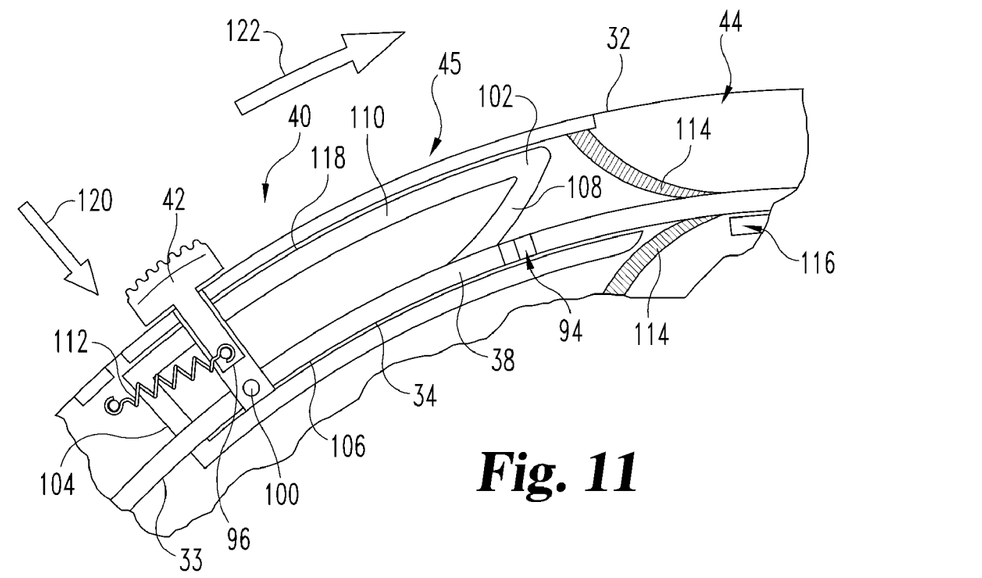
FIG. 11 is a partial, side cross sectional view of the FIG. 10 indexing mechanism.

The indexing mechanism 40 according to one embodiment is illustrated in FIGS. 10 and 11. As shown, the indexing mechanism 40 includes a pair of opposing grip members or grippers 96 that are coupled to or integral with the index button 42. In one form, the grippers 96 are generally spaced apart a fixed distance from one another that roughly corresponds to the width of the test strip tape 38. The grippers 96 each have notch engagement members 98 that face one another and are configured to engage the engagement notches 94 in the test strips 34. Opposite the engagement members 98, the grippers 96 each have guide pins 100 that guide the movement of the grippers 96 during indexing.

Turning to the embodiment of the indexing mechanism 40 shown in FIG. 11, the cartridge 32 has opposing guide or cam grooves 102 that receive and guide the guide pins 100. The cam grooves 102 have different sections that form a somewhat elliptical path so that the grippers 96 move in a cyclic fashion. In particular, each cam groove 102 includes an engagement section 104, an indexing section 106, a disengagement section 108, and a return section 110 that together form a loop. In the illustrated embodiment, the indexing mechanism 40 includes a spring 112 for biasing the grippers 96 in a disengaged position within the engagement section 104. The spring 112 in the embodiment shown is coupled between the index button 42 and the cartridge housing 33. However, the indexing mechanism 40 can incorporate other types of biasing devices, besides the spring 112, or not incorporate any type of biasing device.

To index the test strip tape 38 of the embodiment illustrated in FIG. 11, the user initially presses the button 42 downward (radially inwards relative to the cartridge 32), as indicated by arrow 120 in FIG. 11. As the user presses down the button 42, the guide pins 100 of the grippers 96 slide within the engagement sections 104 of the cam grooves 102 until engagement members 98 of the grippers 96 engage the notches 94 on the test strip tape 38 (FIG. 10). Once the grippers 96 engage the notches 94 on the test strip tape 38, the user pushes the button 42 in an indexing direction, as shown by arrow 122, such that the guide pin 100 moves within the indexing section 106 of the cam groove 102. As the gripper 96 moves in the indexing direction 122, the test strip tape 38 moves such that a new, unused test strip 34 is indexed into position over the contacts 60 of the meter 36 in the sampling notch 44. With reference to FIG. 11, the disengagement section 108 of the cam groove 102 is generally aligned at an oblique angle relative to the indexing section 106. Consequently, as the guide pins 100 slide within the disengagement section 108, the engagement members 98 of the grippers 96 gradually move out of or disengage from the notches 94 in the test strip tape 38, which in turn ceases indexing of the test strip tape 38. Once the guide pins 100 reach the return section 110 of the cam groove 102, the user releases the button 42, and the spring 112 pulls the button 42 back along the return section 110 to its initial position. Additional test strips 34 can be dispensed using the same routine as describe above.

An indexing mechanism 124 according to yet another embodiment will be described with reference to FIGS. 12 and 13. The indexing mechanism 124 in FIG. 12 shares a number of components and features in common with the previously described FIG. 11 indexing mechanism 40, and for the sake of brevity as well as clarity, these common components will not be again described again in great detail below, but reference is made to the previous discussion of these components. The indexing button 42 in the FIG. 12 embodiment has grippers 126 that are resilient and biased to spring apart from one another. The grippers 126 are moveable within a guide channel 128 that includes engagement 130, indexing 132 and disengagement 134 sections. As can be seen, the indexing section 132 is narrower than the engagement 130 and disengagement 134 sections. Due to the resilient nature of the grippers 126, when in the engagement 130 and disengagement 134 sections, the grippers 126 spread apart such that the grippers 126 are not able to engage the test strip tape 38. However, the indexing section 132 is sized to squeeze the grippers 126 together, thereby gripping the notches 94 of the test strip tape 38. It is contemplated that the grippers 126 in other embodiments can be configured to grip the top and bottom surfaces of the test strip tape 38 instead of the side edges.

Figure 12:
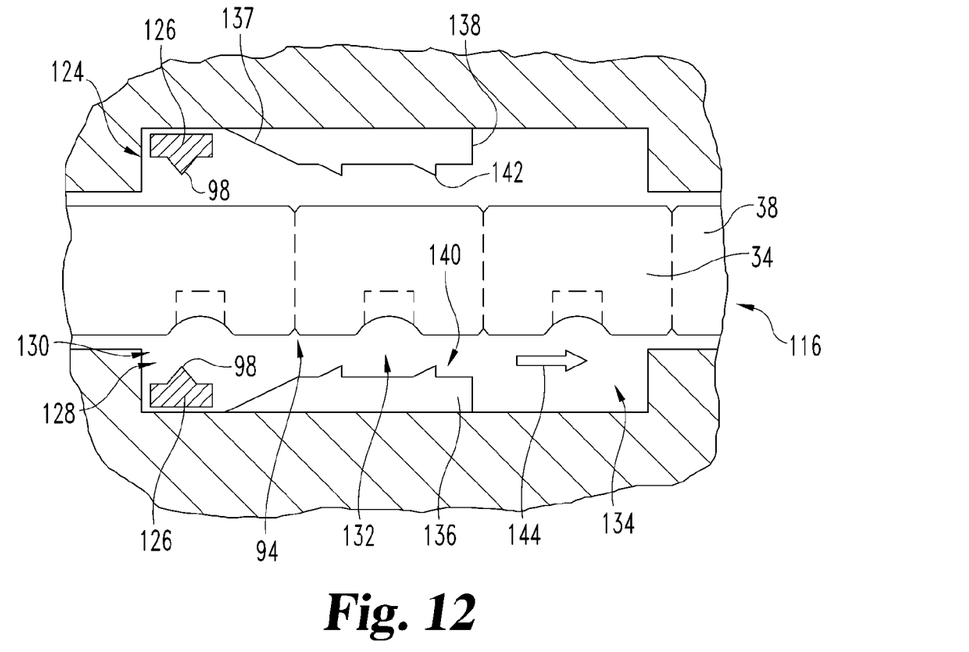
FIG. 12 is a partial, top cross sectional view of an indexing mechanism according to another embodiment.
Figure 13:
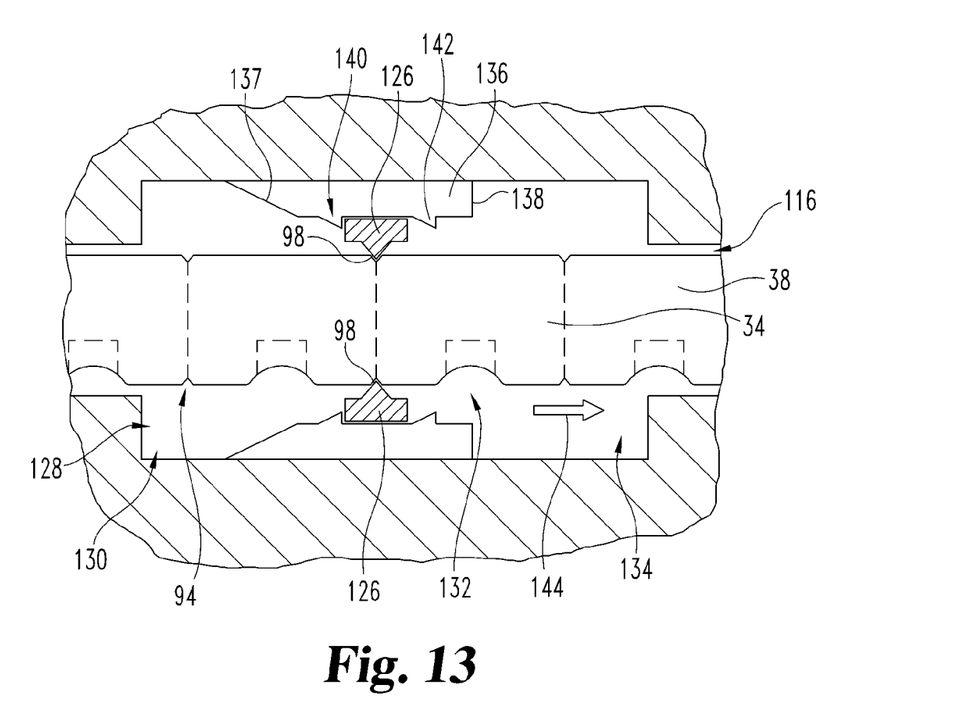
FIG. 13 is a partial, top cross sectional view of the FIG. 12 indexing mechanism in an indexing position.

As illustrated in FIGS. 12 and 13, the indexing section 132 is defined at the bottom of the guide channel 128 by opposing cam members 136. Although not shown in the drawings, the cam members 136 in one embodiment incorporate a retention groove that prevents the grippers 126 from moving vertically out of the indexing section 132, thereby preventing a premature release of the test strip tape 38. As can be seen, the cam members 136 each has a beveled clamping surface 137 between the engagement section 130 and the indexing section 132. The clamping surfaces 137 gradually shrink the size of the guide channel 128 so that the grippers 126 clamp to the test strip tape 38. Next to the disengagement sections 134, the cam members 136 have cut off surfaces 138 that extend generally perpendicular to the other surfaces so as to allow for rapid disengagement of the grippers 126 from the notches 94. In addition, the cut off surfaces 138 prevents the indexing mechanism 124 from operating in a backwards manner. If the test strip tape 38 was allowed to move backwards, a contaminated section of the test strip tape 38 could be drawn back into the cartridge 32.

To further reduce the chance of the indexing mechanism being operated backwards, the indexing mechanism 124 may additionally incorporate a ratchet mechanism 140. As depicted, the ratchet mechanism 140 includes one or more ratchet teeth 142 positioned within the indexing section 132 of the guide channel 128. The ratchet teeth 142 have angled surfaces that permit movement of the grippers 126 in a dispensing direction, as indicated by arrow 144, but the ratchet teeth 142 prevent the grippers 126 from moving in the opposite direction. In the illustrated embodiment, the ratchet teeth 142 are made from a flexible material so as to prevent crushing of the test strip tape 38. It is envisioned that the ratchet mechanism 142 can be configured in other manners so as to prevent or minimize crushing of the test strip tape 38. As should be appreciated, other types of biasing mechanisms can be used to prevent the test strip tape 38 from being indexed backwards.

In order to index the test strip tape 38 of the embodiment illustrated in FIGS. 12 and 13, the user presses on the index button 42 so that the grippers 126 are positioned at the bottom of the guide channel 128 in the engagement section 130. At this position, the grippers 126 are spread apart and are unable to engage the test strip tape 38. The user then pushes the button 42 in the indexing direction 144. The clamping surfaces 137 on the cam members 136 cause the grippers 126 to clamp with the notches 94 in the test strip tape 38. With the grippers 126 clamped to the test strip tape 38, the user is able to index or move the test strip tape 38. Once the grippers 126 reach the larger disengagement section 134, the grippers 126 spring back to their original shape, thereby releasing the test strip tape 38 from the grippers 126. In one embodiment, the button 42 includes one or more springs that bias the button vertically (or radially outward) as well as return the button to its initial location. Once the test strip tape 38 is indexed, the user releases the button 42. Due to the springs, the button pops up vertically such that the grippers 126 are able to move in an unclamped state over the cam members 136 and back to their initial position. The test strip tape 38 can be repeatedly indexed in the same manner as described above. It should be appreciated that the test strip tape 38 can be indexed in other manners. For example, instead of manually indexing the test strips 34, the meter 36 can be configured to automatically index the test strips 34.

An indexing mechanism 150 according to a further embodiment is shown in FIGS. 14, 15, 16, and 17. As will be explained below, the indexing mechanism 150 indexes the test strip tape 38 by frictionally engaging and pushing on the top surface of the tape 38. For the sake of clarity as well as brevity, the various components of the indexing mechanism 150 will not be described in great detail below, but reference is made to U.S. Patent Application Publication No. 2005/0281706 A1 to Funke et al., published Dec. 22, 2005 (U.S. patent application Ser. No. 10/871,943, filed Jun. 18, 2004), which is incorporated by reference in its entirety.

Figure 14:
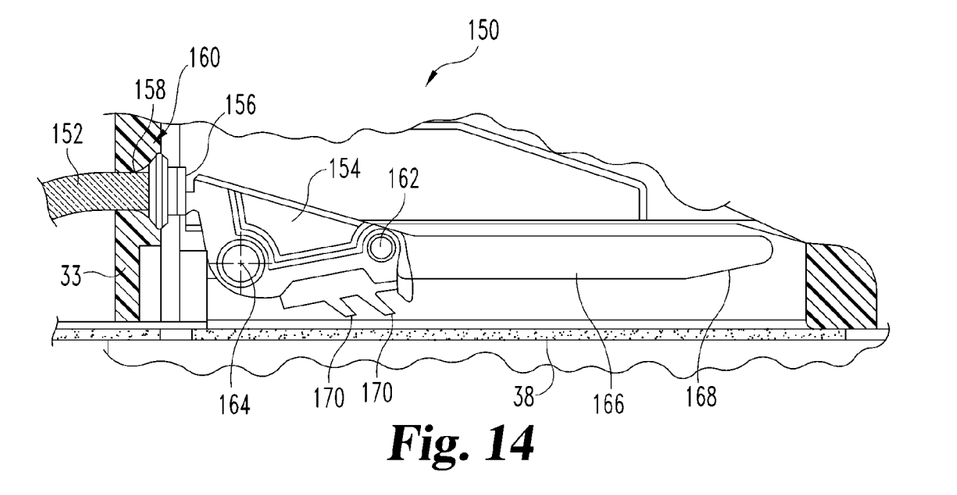
FIG. 14 is a cross sectional view of an indexing mechanism according to a further embodiment with the indexing mechanism in a home position.

As can be seen in FIG. 14, the indexing mechanism 150 includes a flexible arm member 152 and a pusher member or head 154. One end of the flexible arm 152 is coupled to or integrally formed with the indexing button 42, and the other end of the flexible arm is coupled to or integrally formed with the pusher head 154. The pusher head 154 is hingedly connected to the flexible arm 152 by a working hinge 156. The working hinge 156 provides stronger resistance than a normal living hinge, but will still flex, allowing the pusher head 154 to pivot or rotate down onto and up and away from the test strip tape 138. The flexible arm 152 is slidably received in a guide opening 158 that is defined in a guide wall 160 of the cartridge housing 33. In the illustrated embodiment, the flexible arm member 152 is formed from polypropylene, but one of ordinary skill in the art could substitute many other flexible materials.

In the illustrated embodiment, the pusher head 154 has a triangular or L-shaped configuration, but in other embodiments, the pusher head 154 can be shaped differently. At the end opposite the working hinge 156, the pusher head 154 includes opposing guide posts 162. Between the working hinge 156 and the posts 162, the pusher head 154 has cam pins or members 164. Both the posts 162 and the cam pins 164 are slidably disposed in a guide channel or groove 166. At one end, the groove 166 has an inclined surface 168 for disengaging the pusher head 154 from the test strip tape 38. The pusher head 154 has one or more fingers 170 that are configured to frictionally engage the test strip tape 38.

When not in use, the pusher head 154 of the indexing mechanism 150 is positioned in a home position, as is depicted in FIG. 14. A spring or other type of biasing device can be used to bias the pusher head 154 into the home position. While in the home position, the fingers 170 are disengaged from the tape 38. As the user actuates the advancement button 42, the flexible arm 152 slide through the guide opening 158.

Figure 15:
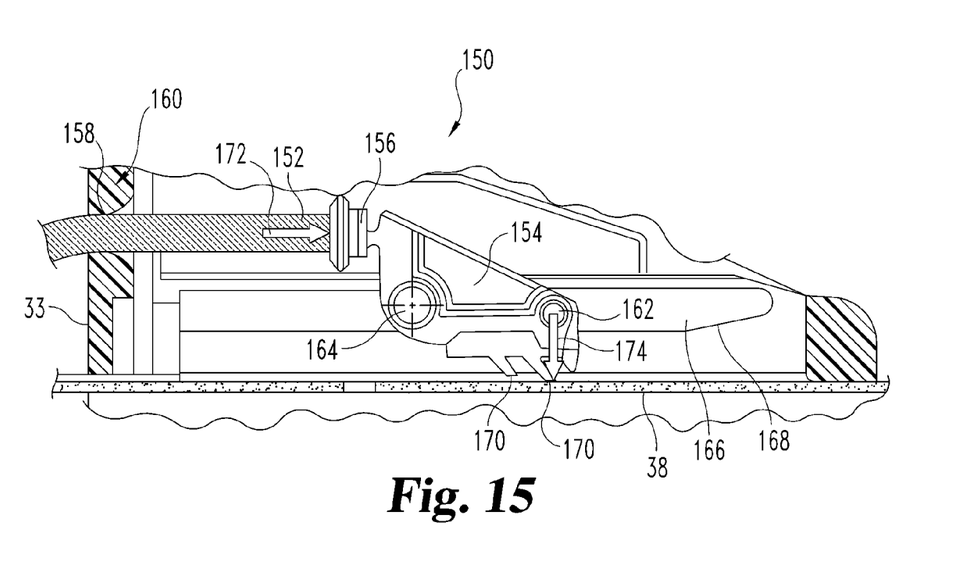
FIG. 15 is a cross sectional view of the FIG. 14 indexing mechanism during an indexing stroke.

Turning now to FIG. 15, this initial movement of the arm 152 causes pusher head 154 to pivot about cams 164. As the pusher head 154 pivots, the fingers 144 frictionally engage the top of the test strip tape 38. In other words, cams 164 define a pivot axis and the sliding movement in the direction of arrow 172 of the flexible arm 152 is translated through working hinge 156 and produces a moment about cams 164. This in turn causes pusher head 154 to pivot down, as shown by arrow 174, such that the fingers 170 engage the tape 38. At the same time, the pusher head 154 slides, thereby indexing the test strip tape 38.

Figure 16:
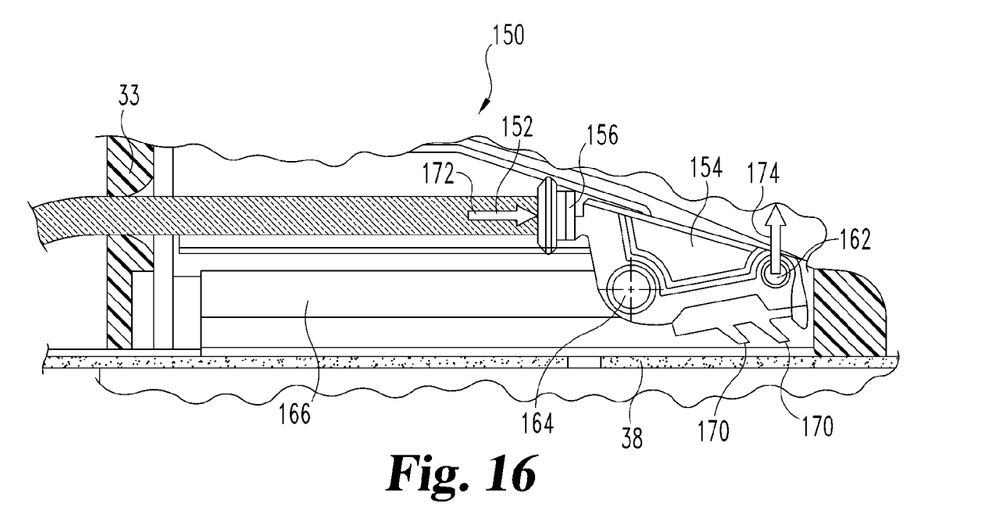
FIG. 16 is a cross sectional view of the FIG. 14 indexing mechanism at the end of the indexing stroke.

Once the pusher head 154 nears the end of the indexing stroke, the posts 142 engage the inclined portion 168 of the guide groove 166, such that the pusher head 154 pivots upward and away from the top test strip tape 38, as shown in FIG. 16. As the pusher head 154 pivots away from the tape 38 in the direction indicated by arrow 174, the fingers 170 release the tape 38, and the indexing movement of the tape 38 ceases.

Figure 17:
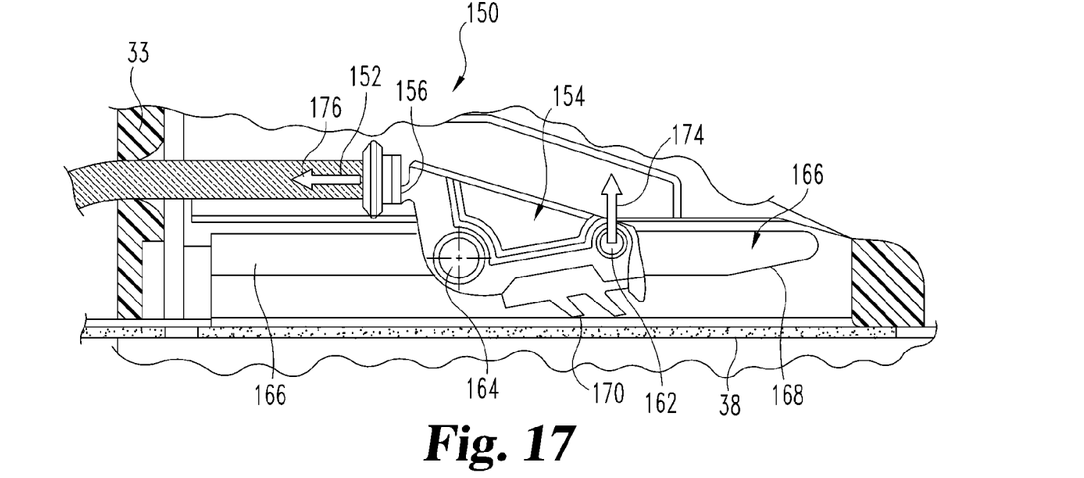
FIG. 17 is a cross sectional view of the FIG. 14 indexing mechanism during a return stroke.

Referring to FIG. 17, when the user releases the advancement button 42, the return spring causes the button 42 and the pusher head 154 to return to the home position, as indicate by arrow 176. On the return stroke, the sliding movement in the direction of arrow 176 of the flexible arm 152 is translated through working hinge 156 and produces a moment about cams 164, which maintains the pusher head 154 in the disengaged position. After the pusher head 154 returns to the home position, the test strip tape can be indexed in a similar fashion as described above.

In order to reduce the chance of contamination, the cartridge 32 has a number of seals that prevent contaminants from entering the cartridge 32. In FIG. 11, a pair of resilient seals 114 seal on opposite sides of the test strip tape 38 near the sampling notch 44 to prevent contaminants from entering through a supply opening 116 of the cartridge 32. Further, a pair of seals 118 is disposed in the advancement slot 45 for sealing around the button 42. To seal the cartridge housing 33, the cartridge housing 33 can be sealed via ultrasonic welding or via a silicone seal. As should be recognized, the cartridge 32 can incorporate other types of sealing structures.

While the invention has been illustrated and described in detail in the drawings and foregoing description, the same is to be considered as illustrative and not restrictive in character. It should be understood that only the preferred embodiment has been shown and described and that all changes and modifications that come within the spirit of the invention are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A portable meter system, comprising:
 a cartridge housing a test strip tape that includes a plurality of test elements, the cartridge defining a meter opening;
 a meter configured to analyze a body fluid via the test strip tape, at least a portion of the meter being received in the meter opening of the cartridge, wherein the portion of the meter includes a projection received in the meter opening, wherein a stop flange extends from one end of the projection;
 wherein the portion of the meter received in the meter opening of the cartridge includes a display that is visible;
 wherein the cartridge encircles the display;
 the cartridge having a sampling portion where the test elements are configured to receive the body fluid;
 the test elements including electrochemical test strips with one or more contacts;
 the meter including one or more contacts coupled to the portion of the meter received inside the meter opening;
 the contacts of the meter being configured to contact the contacts of the electrochemical test strips when at the sampling portion of the cartridge;
 the meter including an alignment key member to which the contacts of the meter are coupled, wherein the alignment key member extends from the projection; and
 the cartridge including an alignment key opening in which the alignment key member is received for aligning the contacts of the meter with the contacts of the electrochemical test strips when positioned within the sampling portion.

2. The system of claim 1, wherein the cartridge includes an indexing mechanism configured to index the test strip tape.

3. The system of claim 2, wherein the test strip tape has at least one indexing notch, the indexing mechanism being configured to engage the test strip tape at the indexing notch.

4. The system of claim 3, wherein:
 the test strip tape has break lines between the test elements for breaking off individual test elements from the test strip tape; and
 the indexing notch is disposed between the test elements adjacent the break lines.

5. The system of claim 3, wherein:
 the indexing member includes a grip member configured to engage indexing notch;
 the cartridge defines a groove for guiding the grip member during indexing; and
 the cam groove is configured to guide the grip member in a direction that is transverse to the test strip tape for engaging the grip member with the indexing notch.

6. The system of claim 3, wherein:
 the indexing member includes a grip member configured to engage indexing notch; and
 the cartridge has a cam member configured to deflect the grip member into engagement with the indexing notch.

7. The system of claim 2, wherein the indexing mechanism includes a pusher member configured to frictionally engage the test strip tape to index the test strip tape.

8. The system of claim 1, wherein the electrochemical test strips each include:
 a first substrate;
 a second substrate;
 a reagent disposed between the first substrate and the second substrate;
 electrodes contacting the reagent between the first substrate and the second substrate; and
 wherein the first substrate defines one or more contact openings along the electrodes that define the contacts of the electrochemical test strips.

9. The system of claim 8, wherein:
 the electrochemical test strips each include a cover layer; and
 the second substrate defines a sample chamber for receiving the body fluid.

10. The system of claim 8, wherein the reagent includes a mesh for rawing the body fluid via capillary action.

11. The system of claim 1, wherein the display is disposed on at least a portion of the projection.

12. The system of claim 11, wherein:
 the meter opening in the cartridge opens on opposite sides of the cartridge;
 the projection of the meter extends completely through the cartridge; and
 the display is disposed on the end of the projection that is opposite the flange.

13. The system of claim 1, wherein the cartridge includes:
 a sampling portion where the test elements are configured to receive the body fluid; and
 a relief indentation at the sampling portion that is concavely shaped to receive a body part.

14. The system of claim 13, wherein each test element includes a relief notch that is concavely shaped similarly to the sampling portion to receive the body part.

15. The system of claim 1, wherein the cartridge includes at least one identifier configured to provide information for calibrating the meter.

16. The system of claim 15, wherein the at least one identifier includes non-evident coding for calibrating the meter.

17. The system of claim 1, wherein the cartridge has a cylindrical outer shape.

18. The system of claim 1, wherein the cartridge includes a coupling flange configured to engage the stop flange of the meter.

19. The system of claim 1, wherein the meter is substantially disposed inside the meter opening of the cartridge.

20. The system of claim 1, wherein:
the cartridge includes means for housing the test strip tape; and
the meter includes electronic means for analyzing the body fluid using electrochemical or optical analysis.

21. The system of claim 1, wherein the cartridge includes:
an advancement slot;
an advancement button slidably disposed along the advancement slot for advancing the test strip tape; and
one or more seals disposed along the advancement slot, the seals being configured to seal against the advancement button.

22. The system of claim 1, wherein the cartridge includes one or more seals sealing against the test strip tape to prevent contaminants from entering the cartridge.

23. A portable meter system, comprising:
a cartridge housing a test strip tape that includes a plurality of test elements, the cartridge defining a meter opening;
a meter configured to analyze a body fluid via the test strip tape, at least a portion of the meter being received in the meter opening of the cartridge;
wherein the portion of the meter received in the meter opening of the cartridge includes a display that is visible;
wherein the cartridge encircles the display;
wherein the cartridge includes an indexing mechanism configured to index the test strip tape;
wherein the test strip tape has at least one indexing notch, the indexing mechanism being configured to engage the test strip tape at the indexing notch;
wherein the indexing member includes a grip member configured to engage indexing notch;
wherein the cartridge defines a groove for guiding the grip member during indexing; and
wherein a cam groove is configured to guide the grip member in a direction that is transverse to the test strip tape for engaging the grip member with the indexing notch.

24. The system of claim 23, wherein the portion of the meter includes a projection received in the meter opening and a stop flange extending from one end of the projection.

25. The system of claim 24, wherein the cartridge includes a coupling flange configured to engage the stop flange of the meter.

26. The system of claim 23, wherein:
the meter opening in the cartridge opens on opposite sides of the cartridge;
the projection of the meter extends completely through the cartridge; and
the display is disposed on the end of the projection that is opposite the flange.

27. The system of claim 23, wherein:
the test strip tape has break lines between the test elements for breaking off individual test elements from the test strip tape; and
the indexing notch is disposed between the test elements adjacent the break lines.

28. A portable meter system, comprising:
a cartridge housing a test strip tape that includes a plurality of test elements, the test elements including electrochemical test strips with one or more contacts, the cartridge having a sampling portion where the test elements are exposed to receive body fluid, the cartridge having an overall ring shape that defines a meter opening with a cylindrical shape, the cartridge having an alignment notch at the meter opening that is aligned with the sampling portion; and
a meter configured to analyze a body fluid via the test strip tape, the meter including
a projection extending through the meter opening in the cartridge,
a stop flange extending from one end of the projection, the stop flange abutting one side of the cartridge to locate the projection inside the meter opening of the cartridge,
the projection having at the end opposite the stop flange a display to display test results, the cartridge housing encircling the display to reduce damage to the display, and
an alignment key member extending from the projection, the alignment key member including one or more contacts, the alignment key member being received in an alignment notch to connect the contacts of the test elements with the contacts of the key member when the test elements are at the sampling portion of the cartridge.

29. The system of claim 28, wherein the cartridge includes an indexing mechanism configured to index the test strip tape.

30. The system of claim 29, wherein the test strip tape has at least one indexing notch, the indexing mechanism being configured to engage the test strip tape at the indexing notch.

31. The system of claim 29, wherein the indexing mechanism includes a pusher member configured to frictionally engage the test strip tape to index the test strip tape.

* * * * *

UNITED STATES PATENT AND TRADEMARK OFFICE
CERTIFICATE OF CORRECTION

PATENT NO. : 7,638,095 B2 Page 1 of 1
APPLICATION NO. : 11/276043
DATED : December 29, 2009
INVENTOR(S) : Peter Sabol It is certified that error appears in the above-identified patent and that said Letters Patent is hereby corrected as shown below:

Col. 12, line 53, replace --mesh for rawing the body fluid via capillary action.-- with "mesh for drawing the body fluid via capillary action."

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,638,095 B2  Page 1 of 1
APPLICATION NO. : 11/276043
DATED : December 29, 2009
INVENTOR(S) : Peter Sabol It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 836 days.

Signed and Sealed this

Ninth Day of November, 2010

David J. Kappos
*Director of the United States Patent and Trademark Office*